(12) United States Patent
Seto

(10) Patent No.: US 8,056,416 B2
(45) Date of Patent: Nov. 15, 2011

(54) ULTRASONIC PROBE, METHOD OF MANUFACTURING THE SAME, AND ULTRASONIC DIAGNOSTIC APPARATUS

(75) Inventor: Yasuhiro Seto, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 640 days.

(21) Appl. No.: 12/059,359

(22) Filed: Mar. 31, 2008

(65) Prior Publication Data

US 2008/0243004 A1    Oct. 2, 2008

(30) Foreign Application Priority Data

Mar. 30, 2007 (JP) ................................. 2007-093465

(51) Int. Cl.
G01N 29/00 (2006.01)
A61B 8/14 (2006.01)
(52) U.S. Cl. .............................. 73/625; 73/632; 600/459
(58) Field of Classification Search .................. 73/625, 73/626, 628, 632; 600/459, 463
See application file for complete search history.

(56) References Cited

U.S. PATENT DOCUMENTS

| | | | | |
|---|---|---|---|---|
| 3,903,380 A | * | 9/1975 | Schomburg ..................... | 324/66 |
| 4,811,740 A | * | 3/1989 | Ikeda et al. .................... | 600/437 |
| 4,901,729 A | * | 2/1990 | Saitoh et al. ................... | 600/459 |
| 4,924,829 A | * | 5/1990 | Cheng et al. ................... | 123/259 |
| 6,605,043 B1 | * | 8/2003 | Dreschel et al. ............... | 600/459 |
| 6,629,928 B1 | * | 10/2003 | Dolan et al. ................... | 600/437 |
| 7,224,104 B2 | * | 5/2007 | Shibamoto et al. ............ | 310/335 |
| 7,249,513 B1 | * | 7/2007 | Zipparo et al. ................. | 73/625 |
| 7,527,591 B2 | * | 5/2009 | Haugen et al. ................. | 600/447 |
| 7,648,459 B2 | * | 1/2010 | Takeda et al. ................. | 600/437 |
| 7,654,961 B2 | * | 2/2010 | Tezuka .......................... | 600/459 |
| 2008/0200812 A1 | * | 8/2008 | Osawa ........................... | 600/459 |
| 2009/0306510 A1 | * | 12/2009 | Hashiba et al. ................ | 600/447 |

FOREIGN PATENT DOCUMENTS

| | | |
|---|---|---|
| JP | 2003-061954 | 3/2003 |
| JP | 2004-229979 A | 8/2004 |

OTHER PUBLICATIONS

Japanese Office Action issued by Japanese Patent Office dated Sep. 13, 2011, corresponding to Japanese Patent Application No. 2007-093465 Partial English language translation.

* cited by examiner

Primary Examiner — Jacques M. Saint Surin
(74) Attorney, Agent, or Firm — Sughrue Mion, PLLC

(57) ABSTRACT

An ultrasonic probe in which cable wiring between transducers within the ultrasonic probe and connector terminals can be simplified. The ultrasonic probe includes: plural ultrasonic transducers for transmitting ultrasonic waves according to supplied drive signals, and receiving ultrasonic echoes to output detection signals; plural terminals provided in a connector to be used for connecting the plural ultrasonic transducers to an ultrasonic diagnostic apparatus main body; plural cables for electrically connecting the plural ultrasonic transducers and the plural terminals to one another; and a storage unit for storing connection relationship data representing connection relationships between the plural ultrasonic transducers and the plural terminals.

9 Claims, 7 Drawing Sheets

ULTRASONIC PROBE, METHOD OF
MANUFACTURING THE SAME, AND
ULTRASONIC DIAGNOSTIC APPARATUS

BACKGROUND OF THE INVENTION

1. Field of the Invention

The present invention relates to an ultrasonic probe to be used for scanning an object to be inspected with ultrasonic waves, and a method of manufacturing the ultrasonic probe. Further, the present invention relates to an ultrasonic diagnostic apparatus using the ultrasonic probe.

2. Description of a Related Art

An ultrasonic probe to be used in an ultrasonic diagnostic apparatus includes an arrayed transducer in which plural ultrasonic transducers for transmitting and receiving ultrasonic waves are one-dimensionally or two-dimensionally arranged. The arrayed transducer and the ultrasonic diagnostic apparatus are connected via a probe cable containing plural thin coaxial cables by using a dedicated connector connected to the arrayed transducer.

The wiring process of the coaxial cables for connecting the arrayed transducer to plural terminals provided on the dedicated connector had required a lot of effort and time because they are connected while correspondences between numbers on the ultrasonic transducers and numbers on the terminals are confirmed by measurement with a tester. Accordingly, the wiring process has been improved by color coding of coaxial cables as disclosed in Japanese Patent Application Publication JP-P2003-61954A.

Recent years, with enhancement of ultrasonic diagnostic technology, the arranged number of arrayed transducers has become increasingly higher, coaxial cables have become thinner, and a number thereof contained in the probe cable has increased. In this regard, even when the color coding of coaxial cables as disclosed in JP-P2003-61954A is applied, the wiring process of the coaxial cables while correspondences between numbers on the ultrasonic transducers and numbers on the terminals are confirmed still requires a lot of effort and time, and therefore, the wiring process problem needs to be solved.

SUMMARY OF THE INVENTION

The present invention has been achieved in view of the above-mentioned situations. A purpose of the present invention is to provide an ultrasonic probe and an ultrasonic diagnostic apparatus in which wiring work in a wiring process of coaxial cables while correspondences between numbers on ultrasonic transducers and numbers on terminals are confirmed using a tester or the like can be eliminated and the wiring work process can be significantly simplified by performing random wiring between the ultrasonic transducers and the connector terminals.

In order to accomplish the purpose, an ultrasonic probe according to one aspect of the present invention includes: plural ultrasonic transducers for transmitting ultrasonic waves according to supplied drive signals, and receiving ultrasonic echoes to output detection signals; plural terminals provided in a connector to be used for connecting the plural ultrasonic transducers to an ultrasonic diagnostic apparatus main body; plural cables for electrically connecting the plural ultrasonic transducers and the plural terminals to one another; and a storage unit for storing connection relationship data representing connection relationships between the plural ultrasonic transducers and the plural terminals.

Further, a method of manufacturing an ultrasonic probe according to one aspect of the present invention includes the steps of: (a) randomly connecting plural ultrasonic transducers and plural terminals, which are provided in a connector to be used for connecting the plural ultrasonic transducers to an ultrasonic diagnostic apparatus main body, to one another via plural cables; (b) receiving a test sound wave signal transmitted from a sound source at the plural ultrasonic transducers to measure reception timing at the plural ultrasonic transducers; (c) creating connection relationship data representing connection relationships between the plural ultrasonic transducers and the plural terminals based on the reception timing at the plural ultrasonic transducers; and (d) storing the connection relationship data in a storage unit of the ultrasonic probe.

Furthermore, an ultrasonic diagnostic apparatus according to one aspect of the present invention is an ultrasonic diagnostic apparatus using an ultrasonic probe including plural ultrasonic transducers, plural terminals provided in a connector to be used for connecting the plural ultrasonic transducers to an ultrasonic diagnostic apparatus main body, plural cables for electrically connecting the plural ultrasonic transducers and the plural terminals to one another, and a storage unit for storing connection relationship data representing connection relationships between the plural ultrasonic transducers and the plural terminals, and the apparatus includes: a transmission and reception circuit for supplying plural drive signals to the plural ultrasonic transducers respectively to cause the plural ultrasonic transducers to transmit ultrasonic waves, and receiving plural detection signals outputted from the plural ultrasonic transducers, which have received ultrasonic echoes, respectively; a connection selecting switch connected between plural terminals provided in a connector to be connected to the ultrasonic probe and the transmission and reception circuit, for switching connection relationships between the plural ultrasonic transducers and the transmission and reception circuit; and control means for controlling the connection relationships in the connection selecting switch based on connection relationship data stored in the storage unit of the ultrasonic probe.

According to the present invention, since wiring work is randomly performed without correspondences between numbers on the transducers and terminal numbers of the connector, the wiring work process can be significantly simplified. As a result, inexpensive ultrasonic probe and ultrasonic diagnostic apparatus can be provided.

DESCRIPTION OF THE PREFERRED EMBODIMENTS

Hereinafter, embodiments of the present invention will be explained in detail with reference to the drawings. The same reference numbers will be assigned to the same component elements and the explanation thereof will be omitted.

In the embodiments as below, the case where an ultrasonic beam is formed by using a linear array having 27 ultrasonic transducers one-dimensionally arranged and simultaneously driving 11 ultrasonic transducers will be explained for simplification of explanation. However, the present invention can also be applied to an array in which plural ultrasonic transducers are two-dimensionally arranged regardless of the number of ultrasonic transducers and the shape of the array.

Figure 1:
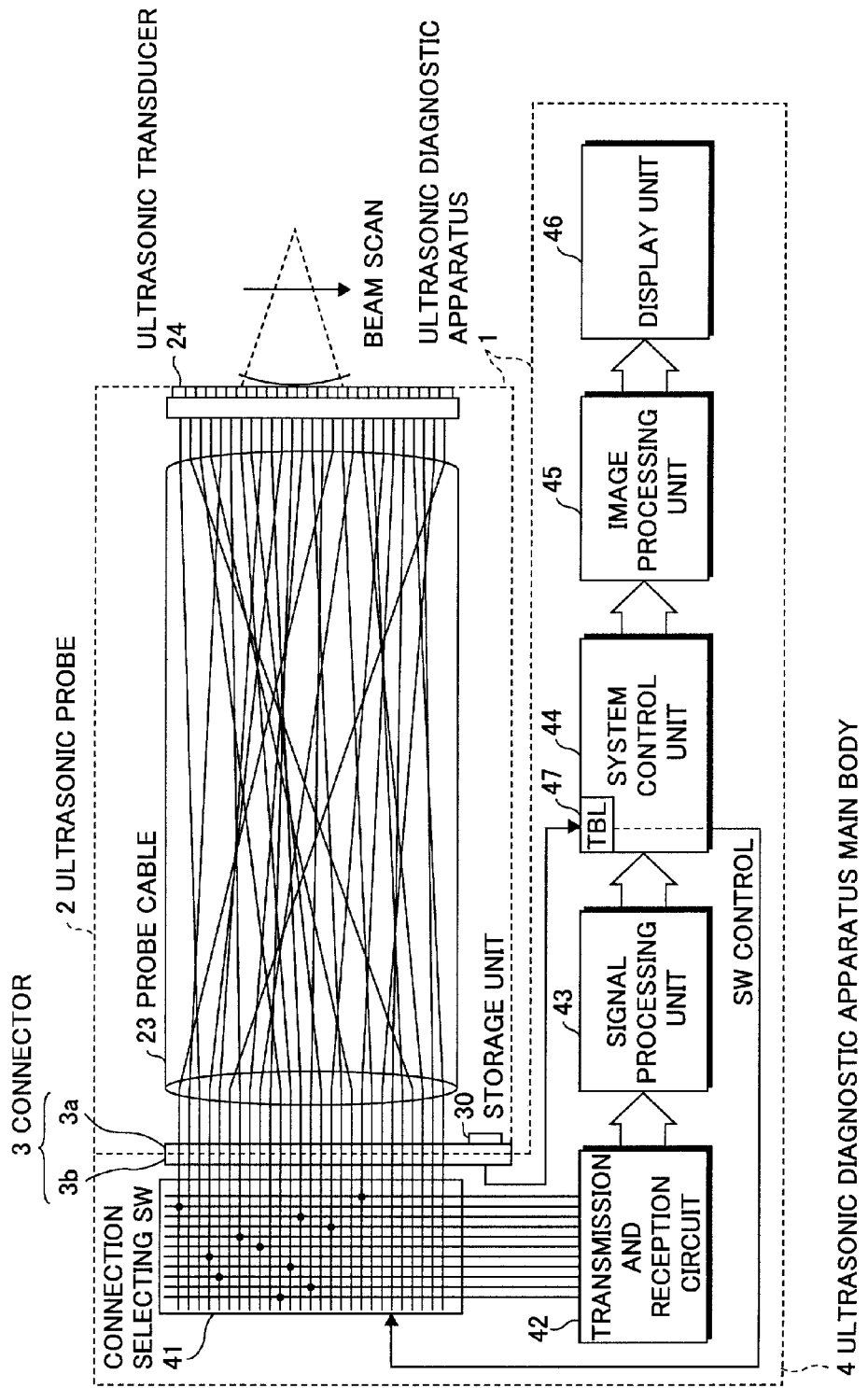
FIG. 1 is a block diagram showing a configuration of an ultrasonic diagnostic apparatus according to one embodiment of the present invention.

FIG. 1 is a block diagram showing a configuration of an ultrasonic diagnostic apparatus according to one embodiment of the present invention using an ultrasonic probe according to one embodiment of the present invention. As shown in FIG. 1, an ultrasonic diagnostic apparatus 1 has an ultrasonic probe 2 and an ultrasonic diagnostic apparatus main body 4 connected to the ultrasonic probe 2 via a connector 3. The connector 3 includes a connector 3a at the ultrasonic probe side and a connector 3b at the ultrasonic diagnostic apparatus main body side, and the connectors 3a and 3b are provided with plural terminals.

The ultrasonic probe 2 has plural ultrasonic transducers 24 for transmitting ultrasonic waves according to supplied drive signals and receiving ultrasonic echoes to output detection signals, and a probe cable 23 containing plural coaxial cables for connecting the ultrasonic transducers 24 to the connector 3a.

As the ultrasonic transducer, for example, a piezoelectric ceramics represented by PZT (Pb(lead) zirconate titanate), a polymeric piezoelectric material represented by PVDF (polyvinylidene difluoride), or the like is used. Further, a piezoelectric element including PZNT (oxide containing lead, zinc, niobium, and titanium) single crystal that has recently been expected to be contributing to improvements in sensitivity and band of ultrasonic transducer may be used.

The ultrasonic diagnostic apparatus main body 4 has a connection selecting switch 41, a transmission and reception circuit 42, a signal processing unit 43, a system control unit 44, an image processing unit 45, and a display unit 46. The ultrasonic diagnostic apparatus main body 4 controls the ultrasonic probe 2 and processes the detection signals outputted from the ultrasonic probe 2 to generate image signals, and thereby, displays an ultrasonic image on the display unit 46.

The connection selecting switch 41 selects the ultrasonic transducers 24 and connects them to the transmission and reception circuit 42. The transmission and reception circuit 42 includes plural transmission circuits and plural reception circuits. The plural transmission circuits generate plural drive signals having delay amounts corresponding to the respective ultrasonic transducers and supply the plural drive signals to the ultrasonic transducers 24 under the control of the system control unit 44. Thereby, a transmission beam is formed, and the ultrasonic probe 2 transmits an ultrasonic beam in a desired direction. The plural reception circuits perform processing such as amplification on plural detection signals outputted from the ultrasonic transducers 24. The transmission circuits are provided for "m" channels from Tx1 to Txm, and the reception circuits 22 are provided for "n" channels from Rx1 to Rxm.

The signal processing unit 43 performs delay processing on the detection signals outputted from the plural reception circuits and adds the delay-processed detection signals to one another. Thereby, reception beam forming is performed. Further, the signal processing unit 43 generates image data based on the added detection signals. The image processing unit 45 performs image processing on the image data outputted from the signal processing unit 43. An ultrasonic image is displayed on the display unit 46 based on the image signals outputted from the image processing unit 45.

Figure 2:
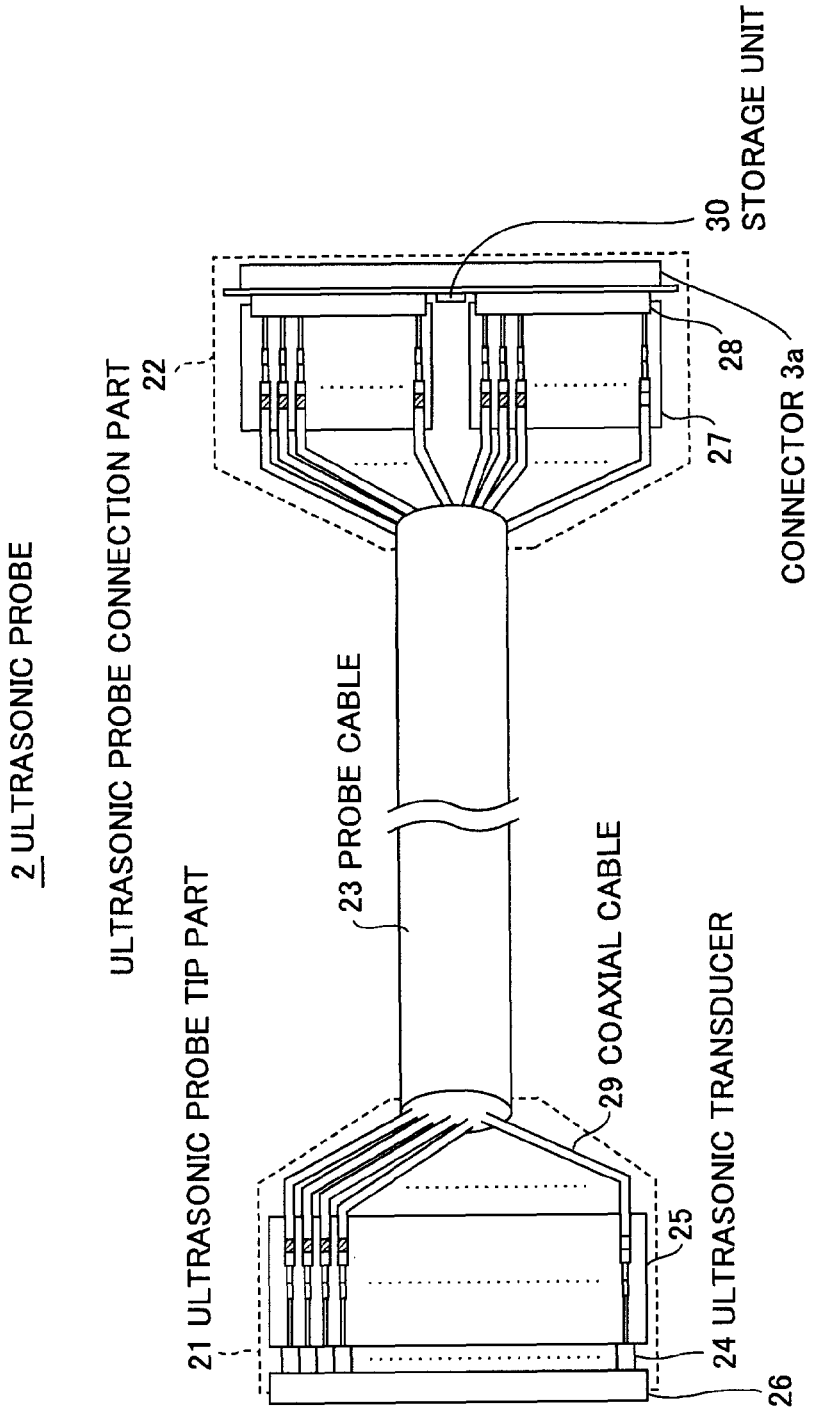
FIG. 2 is a schematic diagram showing a configuration of an ultrasonic probe according to one embodiment of the present invention.

FIG. 2 is a schematic diagram showing a configuration of an ultrasonic probe according to one embodiment of the present invention. The ultrasonic probe 2 has an ultrasonic probe tip part 21 to be used in contact with an object to be inspected, an ultrasonic probe connection part 22 to be connected to the ultrasonic diagnostic apparatus main body 4 (FIG. 1), and a probe cable 23 for connecting between the ultrasonic probe tip part 21 and the ultrasonic probe connection part 22.

The ultrasonic probe tip part 21 has ultrasonic transducers 24 for transmitting and receiving ultrasonic waves, and a flexible printed circuit (FPC) 25 for connecting the ultrasonic transducers 24 to the probe cable 23. The ultrasonic probe tip part 21 may have at least one acoustic matching layer and/or an acoustic lens 26 on the tip ends of the ultrasonic transducers 24.

The ultrasonic probe connection part 22 has a connector 3a to be connected to the ultrasonic diagnostic apparatus main body 4. Furthermore, the ultrasonic probe connection part 22 may have a relay substrate 27 for connecting the connector 3a to the probe cable 23, and may have an intermediate connector 28 between the connector 3a and the relay substrate 27. The ultrasonic probe connection part 22 includes a storage unit 30 such as a nonvolatile memory for storing connection relationship data explained as below. As the nonvolatile memory, a serial access type EEPROM (Electrically Erasable Programmable ROM), flash memory, or the like is used. The probe cable 23 contains plural coaxial cables 29.

Next, the wiring connection work process of the coaxial cables 29 of the ultrasonic probe 2 shown in FIG. 2 will be explained. Since the length of the coaxial cable 29 is about 2.5 m in an ultrasonic probe for body surface and 3 m or more in an ultrasonic probe for endoscope, a complicated process is needed for management of wiring order of coaxial cables at the time of wiring work.

Accordingly, in the embodiment, in order to simplify the complicated process, the plural coaxial cables 29 for connecting the plural ultrasonic transducers 24 and the plural terminals of the connector 3a to one another are irregularly connected in a random manner without taking one-to-one correspondences between the numbers on the ultrasonic transducers 24 and the numbers on the terminals.

Specifically, first, the first terminal of the plural coaxial cables 29 is randomly connected to the signal lead part of the flexible printed circuit 25, to which the plural ultrasonic transducers 24 have been connected, by soldering without regard to colors and order. Then, the second terminal of the plural coaxial cables 29 is randomly connected to the plural terminals of the connector 3a without regard to the number of the ultrasonic transducer 24 to which the first terminal of the coaxial cables 29 has been connected. Actually, the coaxial cables 29 are not directly connected to the terminals of the connector 3a, but the relay substrate 27 and the intermediate connector 28 for connecting coaxial cables are generally used.

Typically, operation check is performed on the respective ultrasonic transducers 24 of the completed probe 2 by using a special inspection and determination unit. In the embodiment, arrangement numbers of the respective ultrasonic transducers 24 on the array are checked prior to the operation check, and connection relationship data, which represents how the randomly connected plural ultrasonic transducers 24 and the plural terminals of the connector 3a have been actually connected, is created and stored in the storage unit 30 of the ultrasonic probe 2.

As below, a measurement method of the connection relationships of ultrasonic transducers will be explained.

Figure 3:
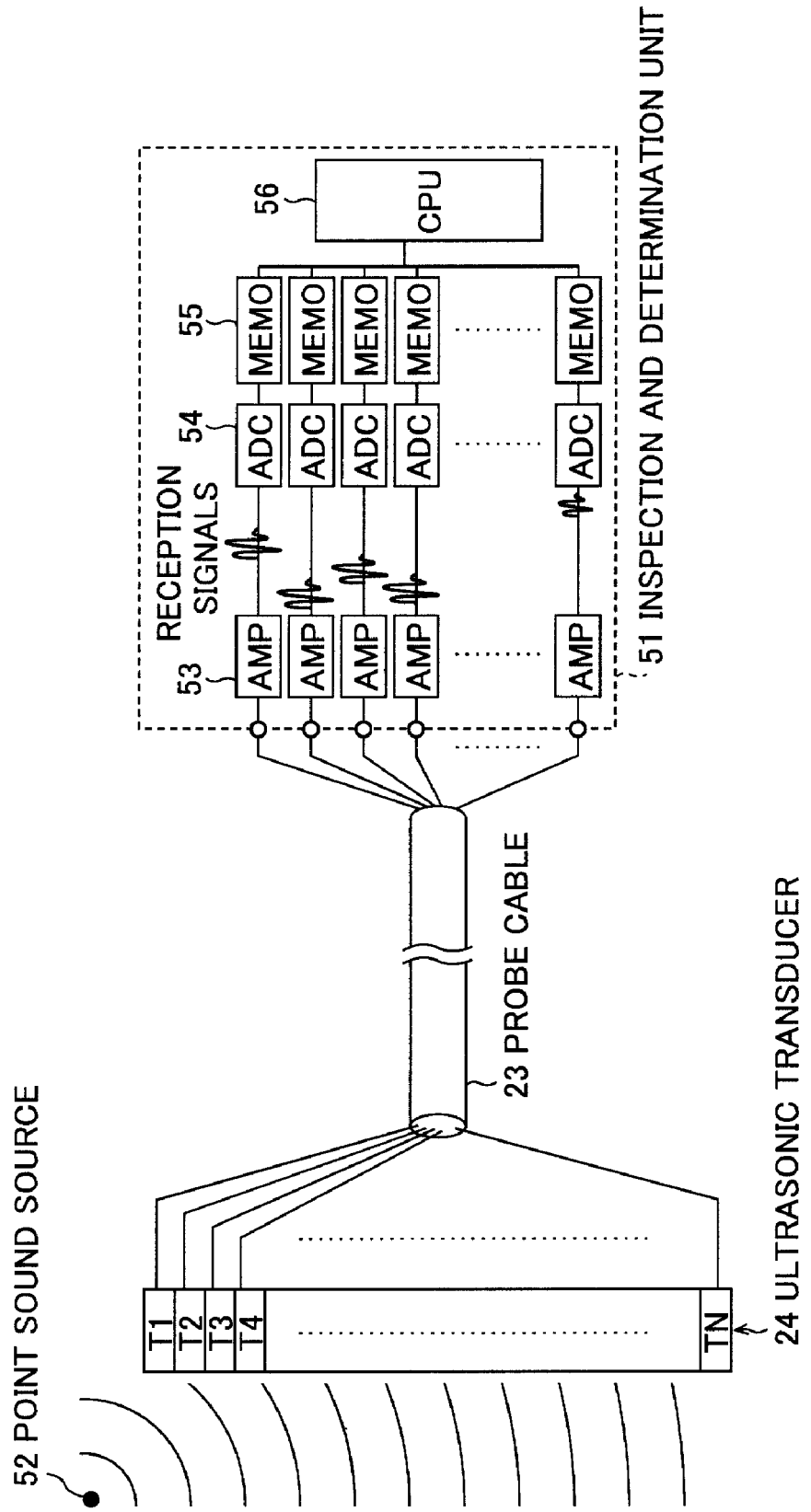
FIG. 3 is a diagram for explanation of a method of measuring connection relationships of ultrasonic transducers by using a fixed point sound source.

FIG. 3 is a diagram for explanation of a method of measuring the connection relationships of ultrasonic transducers by using a fixed point sound source. As shown in FIG. 3, the ultrasonic probe 2 to be measured about the connection relationships of ultrasonic transducers is connected to an inspection and determination unit 51 via a connector.

The inspection and determination unit 51 has a phantom in which a point sound source 52 is provided in an acoustic medium, amplifiers (AMPs) 53 for amplifying the detection signals outputted from the independent ultrasonic transducers 24 that receive a test sound wave signal (pulsed ultrasonic waves) transmitted from the point sound source 52, A/D converters (ADCs) 54 for A/D converting the amplified detection signals outputted from the amplifiers 53 to output detection data, memory devices (MEMOs) 55 such as a memory for storing the detection data outputted from the A/D converters 54, and a control unit (CPU) 56 for controlling the respective parts, loading connection relationship data stored in the storage unit 30 (FIG. 2) within the ultrasonic probe 2, and writing connection relationship data in the storage unit 30.

The control unit 56 detects reception timing at the plural ultrasonic transducers 24 based on the detection data stored in the memory devices 55, determines the connection relationships of the plural ultrasonic transducers 24 based on the detected reception timing, and thereby, creates connection relationship data representing the connection relationships between the plural ultrasonic transducers 24 and the plural terminals of the connector 3a (FIG. 2), and writes the connection relationship data in the storage unit 30 (FIG. 2) within the ultrasonic probe 2.

As shown in FIG. 3, since the point sound source 52 is provided at the upper end of the arrayed transducer, it can be determined that the lowermost terminal, which receives the test sound wave signal at the earliest time, is connected to the ultrasonic transducer T1. Subsequently, it can be determined that the uppermost terminal, which receives the test sound wave signal at the second earliest time, is connected to the ultrasonic transducer T2. In this manner, the connection relationships of the ultrasonic transducers connected to the respective terminals can be specified by checking the reception timing at all terminals.

In the adjacent two ultrasonic transducers, the larger the distance difference between the ultrasonic transducer and the point sound source, the larger the reception timing difference of the ultrasonic transducers, and thus, the connection relationships are specified more easily. Contrary, in the case of the sound source position shown in FIG. 3, it is difficult to specify the connection relationships of the ultrasonic transducers near the upper end. This problem is solved by measuring the reception timing of the plural ultrasonic transducers 24 and determining the connection relationships in the sound source position shown in FIG. 3, and then, moving the point sound source 52 to the lower end of the array transducer, and then, measuring the reception timing of the plural ultrasonic transducers 24 and determining the connection relationships, and judging the plural connection relationship determination results at different positions of the point sound source 52 in combination. Thus, correct connection relationship data can be obtained.

In the above explained fixed point sound source system, in the case where the plural ultrasonic transducers are arranged in a convex form with a large angle, there may be an ultrasonic transducer which ultrasonic waves do not reach. Further, even in the case where the plural ultrasonic transducers are arranged in a linear form, when the number of ultrasonic transducers is large, the attenuation in the acoustic lens is great and there may be an ultrasonic transducer that can receive only a feeble test sound wave signal. In this case, it is difficult to specify the connection relationship according to the fixed point sound source method.

Figure 4:
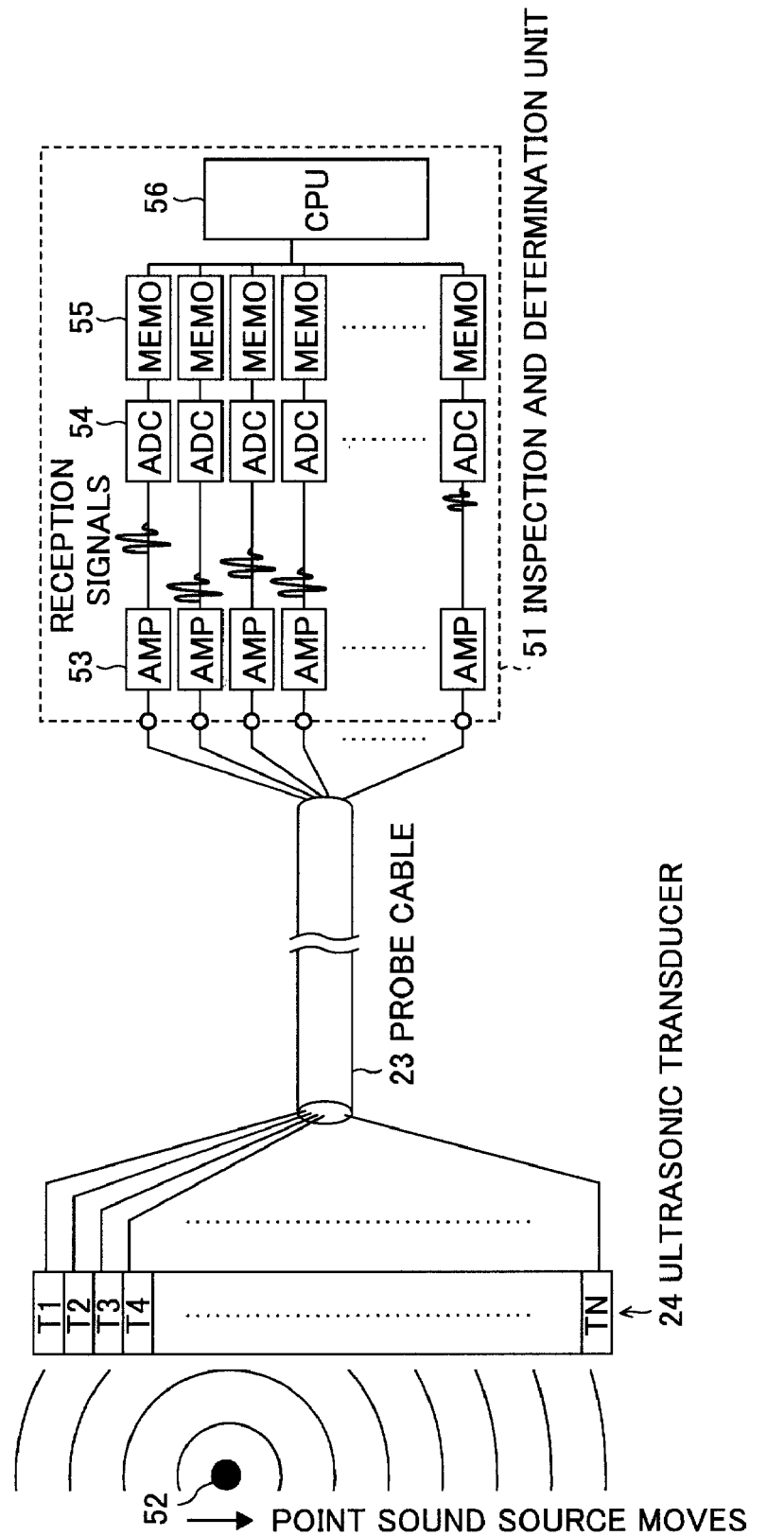
FIG. 4 is a diagram for explanation of a method of measuring connection relationships of ultrasonic transducers by using a moving point sound source.

FIG. 4 is a diagram for explanation of a method of measuring the connection relationships of ultrasonic transducers by using a moving point sound source. As shown in FIG. 4, the reception timing can be correctly measured even in the above-mentioned case by moving the point sound source 52 along the transmission surface of the arrayed transducer and measuring the reception timing at each time when the point sound source is moved by 1/N (N is an integral number) times the arrangement pitch of the plural ultrasonic transducers. Therefore, the connection relationship of the ultrasonic transducers can be specified.

In the above explanation, the point sound source provided outside of the ultrasonic probe has been used. However, the connection relationship of the ultrasonic transducers may be specified by providing a reflector in place of the point sound source, transmitting pulsed ultrasonic waves from at least one ultrasonic transducer, and measuring the reception timing of the ultrasonic waves reflected by the reflector.

Further, in the case shown in FIG. 3, since the reception timing of the ultrasonic transducer T1 is the earliest, when the wire of the ultrasonic transducer T1 is known by color coding or the like, the connection relationships of the plural ultrasonic transducers can be specified by measuring the delay times of reception timing at the other ultrasonic transducers with the reception timing at the ultrasonic transducer T1 as reference.

Further, in the case where the plural coaxial cables contained in the probe cable 23 are connected, it is no hindrance of wiring process but an advantage for simplification of wiring process that only the wire of the ultrasonic transducer located at the upper end or lower end or the wires of the ultrasonic transducers at both ends may be distinguished by color-coding or the like, and the certain wire is connected to the certain connector terminal by identifying the wire.

In this manner, by distinguishing only the wire of the certain ultrasonic transducer among the random cable wiring, the reference for determination of the connection relationships of the rest of the ultrasonic transducers can be set and the measurement of connection relationships of the ultrasonic transducers can be efficiently performed.

Further, according to the connection relationships of ultrasonic transducers, the determination of connection relationships may be secured by dividing plural acoustic cables connected to the ultrasonic transducers into plural groups and leading out the cables to increase the distances between adjacent two ultrasonic transducers in one group.

Figure 5:
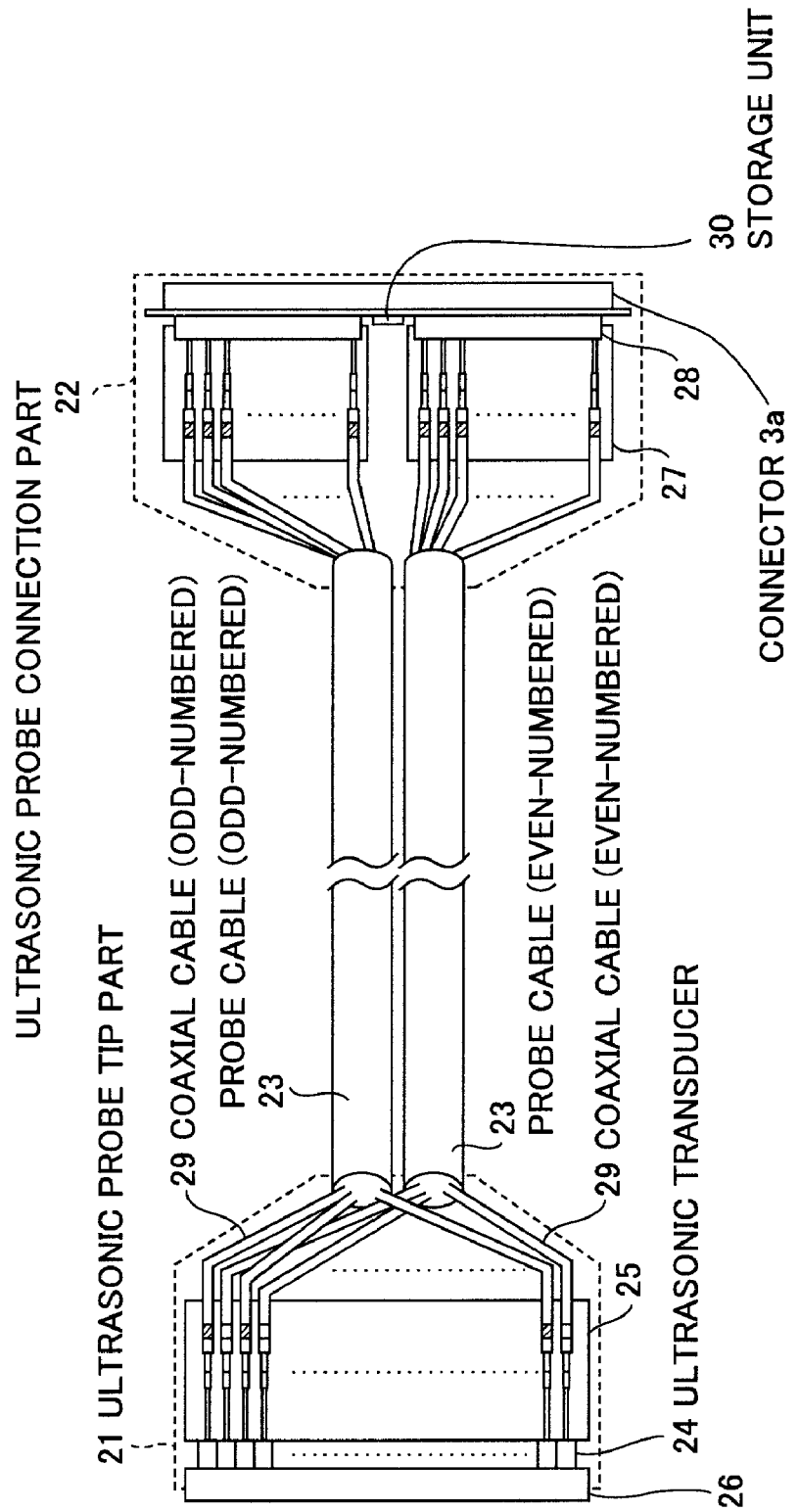
FIG. 5 is a schematic diagram showing a configuration of an ultrasonic probe with wiring divided in two according to one embodiment of the present invention.

For example, as shown in FIG. 5, according to whether the connection relationships of ultrasonic transducers are odd-numbered or even-numbered, the plural coaxial cables connected to the ultrasonic transducers are divided into two groups. Thereby, correct measurement of the difference in reception timing of adjacent two ultrasonic transducers becomes easier. In this regard, as shown in FIG. 5, on the flexible printed circuit 25, a pattern to which odd-numbered ultrasonic transducers are connected may be provided on the front side and a pattern to which even-numbered ultrasonic transducers are connected may be provided on the reverse side.

Next, an operation of the ultrasonic diagnostic apparatus according to one embodiment of the present invention will be explained with reference to FIG. 1. In the ultrasonic probe 2, plural ultrasonic transducers 24 are randomly connected to plural terminals of the connector 3a via plural cables 23. The ultrasonic probe 2 is connected to the ultrasonic diagnostic apparatus main body 4 via the connector 3.

Since the ultrasonic probe 2 adapted for diagnostic purpose is used at the time of ultrasonic diagnosis, the ultrasonic diagnostic apparatus main body 4 loads connection relationship data stored in the storage unit 30 of the ultrasonic probe 2 and controls the transmission and reception circuit 42 based on the connection relationship data, and thereby, transmits and receives ultrasonic waves.

The electronic scan method in the ultrasonic diagnostic apparatus 1 is to supply drive signals provided with desired delays to the plural ultrasonic transducers to make them perform transmission operations having time differences, and thus, form an ultrasonic beam focusing on one focal point, and to provide desired delays to plural detection signals outputted from the plural ultrasonic transducers and add them to one another to form one focal point in received ultrasonic echoes. By moving the focal point, the entire imaging region of the object is scanned. In ultrasonic beam forming operation, "sparse array" using only part of ultrasonic wave detection elements of plural ultrasonic wave detection elements may be used.

Figure 6:
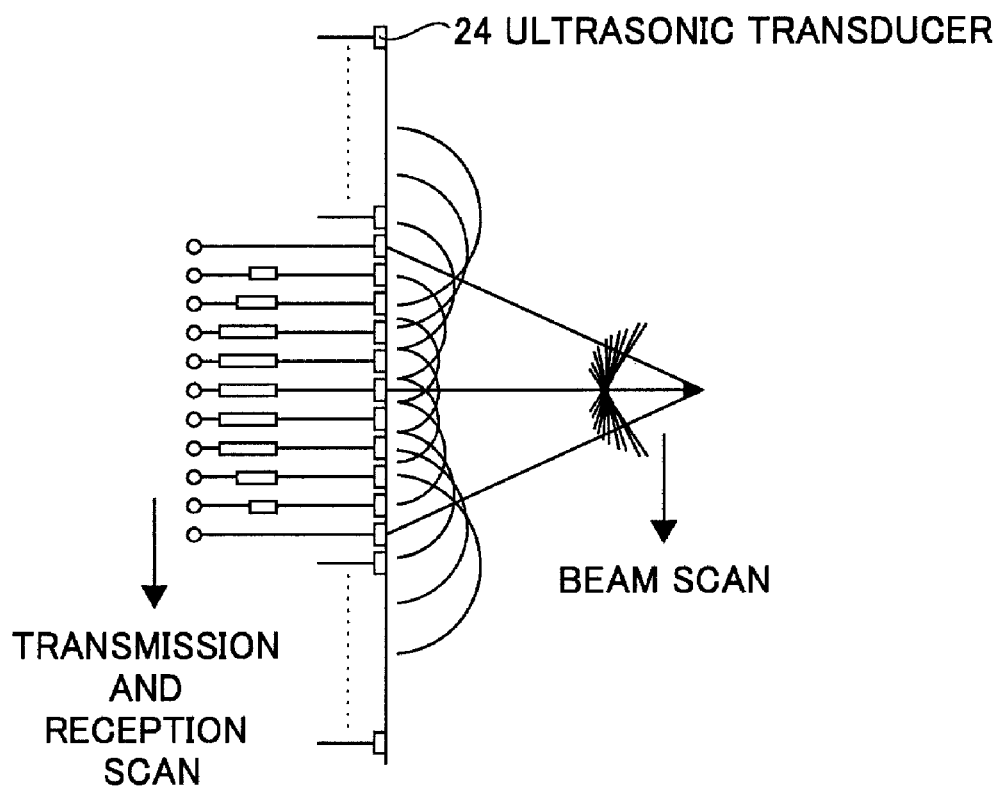
FIG. 6 is a diagram for explanation of ultrasonic beam forming operation.

FIG. 6 is a diagram for explanation of ultrasonic beam forming operation when a 27 channel array is simultaneously driven with an 11-channel transmission circuit. That is, ultrasonic transducers to be used for one transmission or reception are part of the entire array. Accordingly, in the ultrasonic diagnostic apparatus main body 4, transmission and reception circuits in the same number as the number of ultrasonic transducers to be connected are mounted, and scan is performed while connections between ultrasonic transducers and transmission and reception circuits are switched with respect to each transmission or reception. Also, in this case, as shown in FIG. 1, the connection selecting switch 41 such as a cross-point switch is provided between the ultrasonic probe connector 3 and the transmission and reception circuits 42, and ultrasonic transmission and reception of ultrasonic waves are performed while the connection selecting switch 41 switches connection between the transmission and reception circuits 42 and the ultrasonic transducers 24 based on the connection relationship data.

Figure 7:
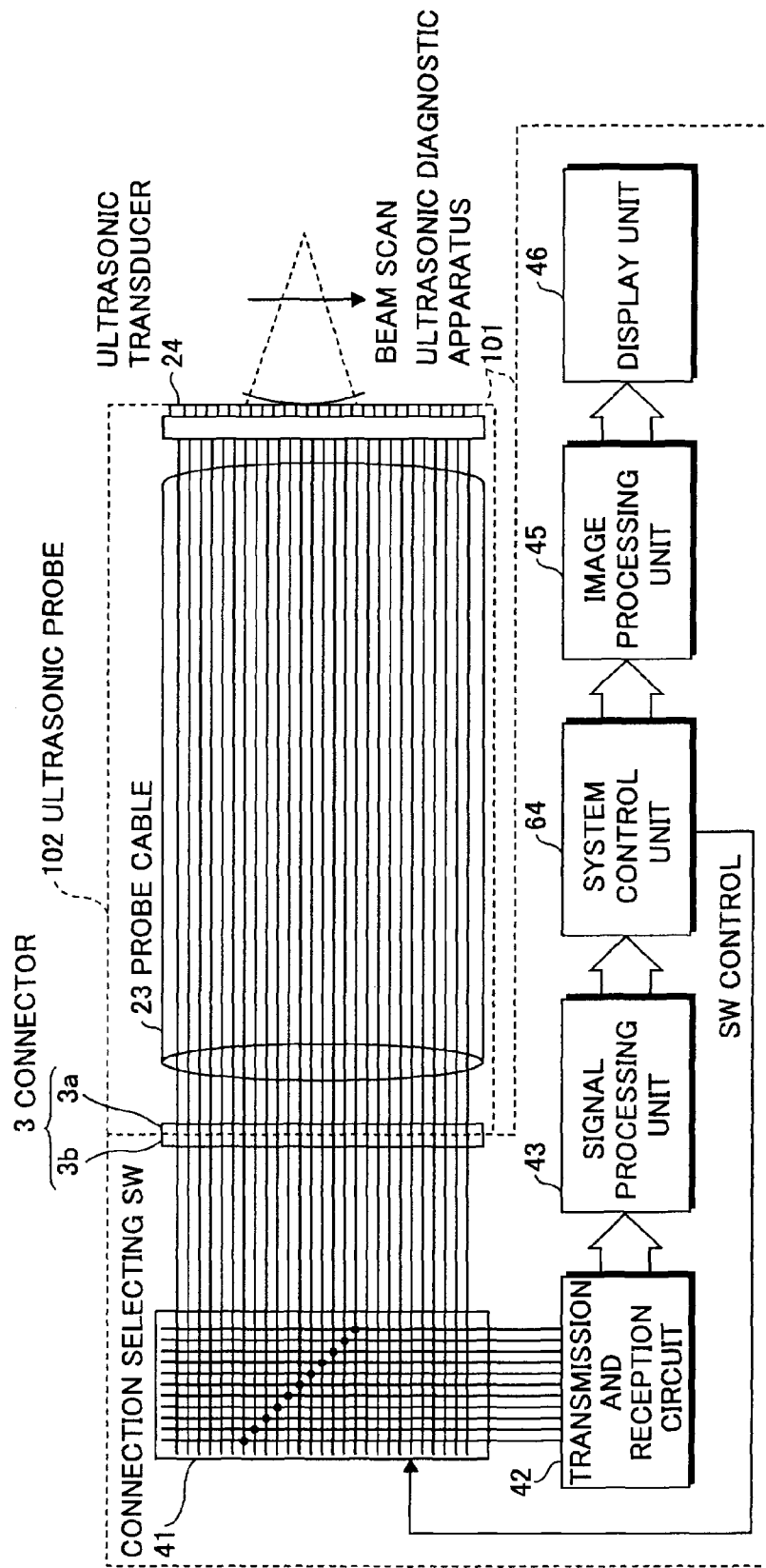
FIG. 7 is a block diagram showing a configuration example of a conventional ultrasonic diagnostic apparatus.

In a conventional ultrasonic diagnostic apparatus 101 shown in FIG. 7, since correspondences between numbers on the ultrasonic transducers 24 and terminal numbers of the connector 3a are confirmed within an ultrasonic probe 102 and those are regularly connected via the probe cable 23, a system control unit 64 of an ultrasonic diagnostic apparatus 104 controls the connection selecting switch 41 according to the setting, and thus, desired ultrasonic transducers are connected.

On the other hand, in the ultrasonic diagnostic apparatus 1 according to one embodiment of the present invention shown in FIG. 1, since no correspondences between numbers on the ultrasonic transducers 24 and terminal numbers of the connector 3a are confirmed and those are randomly connected by the probe cable 23, it is necessary for the system control unit 44 of the ultrasonic diagnostic apparatus main body 4 to obtain connection relationship data representing connection relationships between the plural ultrasonic transducers 24 and the plural terminals of the connector 3a.

Accordingly, as shown in FIG. 1, the connection relationship data of the ultrasonic transducers 24 is stored in the storage unit 30 such as a nonvolatile memory within the ultrasonic probe 2. When the ultrasonic probe 2 is connected to the ultrasonic diagnostic apparatus main body 4, the system control unit 44 of the ultrasonic diagnostic apparatus main body 4 loads the connection relationship data from the storage unit 30 within the ultrasonic probe 2, creates a conversion table (TBL) 47 for correspondences between numbers on ultrasonic transducers and numbers on terminals, and stores it in a storage unit such as a memory within the system control unit 44. When ultrasonic beam scan is performed, the system control unit 44 refers to the connection relationship data in the conversion table 47 and controls the connection selecting switch 41, and thereby, connects the desired ultrasonic transducers 24 to the transmission and reception circuit 42.

In the storage unit 30 within the ultrasonic probe 2, characteristic data, correction data, and so on corresponding to independent ultrasonic transducers are stored in addition to the connection relationship data on connection of ultrasonic transducers, and various conditions in transmission operation, signal processing, and image processing for acquiring ultrasonic diagnostic images may be set. The items to be set are, for example, array form, number of array elements, operation frequency, transmission pulse voltage, reception gain, contrast, STC (sensitivity time gain control) characteristic, $\gamma$ characteristic, and so on. Further, in the case where the ultrasonic probe already has a storage unit for storing characteristic data or correction data, it can be realized without cost increase by adding connection relationship data into the existing storage unit.

The invention claimed is:

1. An ultrasonic probe to be used by being connected to an ultrasonic diagnostic apparatus main body, said ultrasonic probe comprising:
  plural ultrasonic transducers for transmitting ultrasonic waves according to supplied drive signals, and receiving ultrasonic echoes to output detection signals;
  plural terminals provided in a connector to be used for connecting said ultrasonic probe to said ultrasonic diagnostic apparatus main body;
  plural cables for electrically connecting said plural ultrasonic transducers and said plural terminals respectively; and
  a storage unit for storing connection relationship data representing connection relationships between said plural ultrasonic transducers and said plural terminals,
  wherein said plural ultrasonic transducers and first ends of said plural cables are randomly connected to one another, and second ends of said plural cables and said plural terminals are randomly connected to one another.

2. An ultrasonic probe to be used by being connected to an ultrasonic diagnostic apparatus main body, said ultrasonic probe comprising:
  plural ultrasonic transducers for transmitting ultrasonic waves according to supplied drive signals, and receiving ultrasonic echoes to output detection signals;
  plural terminals provided in a connector to be used for connecting said ultrasonic probe to said ultrasonic diagnostic apparatus main body;
  plural cables for electrically connecting said plural ultrasonic transducers to said plural terminals respectively; and a storage unit for storing connection relationship data representing connection relationships between said plural ultrasonic transducers and said plural terminals, wherein said plural terminals include a first group of terminals in a first region and a second group of terminals in a second region;

said plural cables include first group of cables and a second group of cables; and odd-numbered ultrasonic transducers of said plural ultrasonic transducers are connected to first ends of said first group of cables, even-numbered ultrasonic transducers of said plural ultrasonic transducers are connected to first ends of said second group of cables, second ends of said first group of cables are connected to said first group of terminals, and second ends of said second group of cables are connected to said second group of terminals.

3. The ultrasonic probe according to claim 1, wherein said storage unit includes a nonvolatile memory.

4. A method of manufacturing an ultrasonic probe to be used by being connected to an ultrasonic diagnostic apparatus main body, said method comprising the steps of:
   (a) randomly connecting plural ultrasonic transducers to plural terminals, which are provided in a connector to be used for connecting said plural ultrasonic probe to said ultrasonic diagnostic apparatus main body, respectively via plural cables;
   (b) receiving a test sound wave signal transmitted from a sound source at said plural ultrasonic transducers to measure reception timing at said plural ultrasonic transducers;
   (c) creating connection relationship data representing connection relationships between said plural ultrasonic transducers and said plural terminals based on the reception timing at said plural ultrasonic transducers; and
   (d) storing said connection relationship data in a storage unit of said ultrasonic probe.

5. The method according to claim 4, wherein said sound source is a fixed sound source.

6. The method according to claim 4, wherein said sound source is a moving sound source.

7. The method according to claim 4, wherein step (b) includes the steps of:

transmitting a test sound wave signal from at least one of said plural ultrasonic transducers to be used as said sound source; and receiving the test sound wave signal reflected by a reflector provided before a transmission surface of said plural ultrasonic transducers at said plural ultrasonic transducers to measure reception timing at said plural ultrasonic transducers.

8. The method according to claim 4, wherein said storage unit includes a nonvolatile memory.

9. An ultrasonic diagnostic apparatus comprising:

an ultrasonic probe including plural ultrasonic transducers, plural terminals provided in a connector to be used for connecting said plural ultrasonic probe to an ultrasonic diagnostic apparatus main body, plural cables for electrically connecting said plural ultrasonic transducers to said plural terminals respectively, and a storage unit for storing connection relationship data representing connection relationships between said plural ultrasonic transducers and said plural terminals, wherein said plural ultrasonic transducers and first ends of said plural cables are randomly connected to one another, and second ends of said plural cables and said plural terminals are randomly connected to one another;

a transmission and reception circuit for supplying plural drive signals to said plural ultrasonic transducers respectively to cause said plural ultrasonic transducers to transmit ultrasonic waves, and receiving plural detection signals outputted from said plural ultrasonic transducers, which have received ultrasonic echoes, respectively;

a connection selecting switch connected between plural terminals provided in a connector to be connected to said ultrasonic probe and said transmission and reception circuit, for switching connection relationships between said plural ultrasonic transducers and said transmission and reception circuit; and control means for controlling the connection relationships in said connection selecting switch based on connection relationship data stored in said storage unit of said ultrasonic probe.

* * * * *